Figure 1:
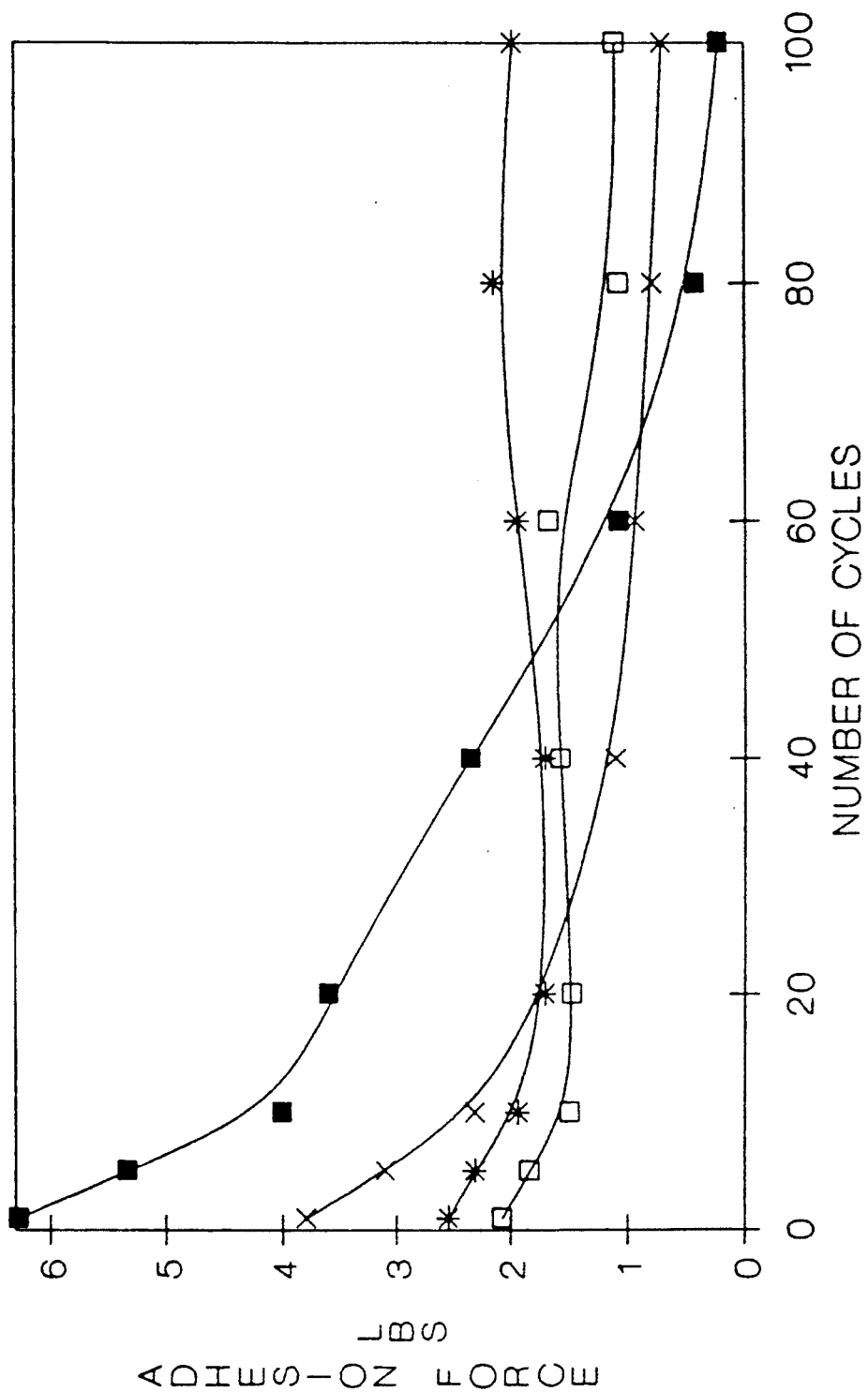

United States Patent [19]
Prosise et al.

[11] Patent Number: 5,298,534
[45] Date of Patent: Mar. 29, 1994

[54] DENTURE ADHESIVE

[75] Inventors: William E. Prosise, Ramsey; Mahmoud Amin, Flemington, both of N.J.

[73] Assignee: ISP Investments Inc., Wilmington, Del.

[21] Appl. No.: 24,135

[22] Filed: Mar. 1, 1993

[51] Int. Cl.$^5$ .................. A61C 13/23; C08L 93/00
[52] U.S. Cl. ................... 523/120; 523/118; 524/55
[58] Field of Search .......... 523/118, 120, 116; 524/55

[56] References Cited

U.S. PATENT DOCUMENTS

| | | | |
|---|---|---|---|
| 4,393,080 | 7/1983 | Pawelchak et al. | 523/118 |
| 4,470,814 | 9/1984 | Chang et al. | 523/120 |
| 4,521,551 | 6/1985 | Chang et al. | 523/120 |
| 5,093,387 | 3/1992 | Schobel et al. | 524/55 |

OTHER PUBLICATIONS

Encyclopedia of Chemical Technology, Third Edition, John Wiley & Sons, vol. 12.

Primary Examiner—Paul R. Michl
Assistant Examiner—Peter Szekely
Attorney, Agent, or Firm—Marilyn J. Maue; Joshua J. Ward

[57] ABSTRACT

This invention relates to an improved adhesive composition having extended holding power accompanied by adhesion building properties during use and having increased gel adhesion, which composition consists essentially of (a) from about 10 to about 35 wt. % lower alkyl vinyl ether-maleic acid copolymer wherein from 0 to about 90 wt. % of the copolymer carboxyl units are converted to a mixture of salts selected from the group of calcium, sodium, strontium, zinc, magnesium and potassium; (b) a crosslinked non-ionic natural guar gum in a mole ratio of between about 0.75:1 and about 5:1 with respect to the copolymer; and (c) from about 30 to about 70 wt. % oil base as a carrier. The invention also relates to the preparation and use of said adhesive for affixing dentures.

17 Claims, 4 Drawing Sheets

DENTURE ADHESIVE

In one aspect the present invention relates to an improved adhesive composition which provides extended effective holding power and in another aspect, the invention pertains to the use of said composition as an improved denture adhesive.

BACKGROUND OF THE INVENTION

Various adhesive compositions have been employed for affixing dentures or ostomy devices to mucus membranes, several of which involve the use of methyl vinyl ether-maleic acid metal salts as disclosed in U.S. Pat. Nos. 3,003,988; 3,833,518; 3,868,339; 4,758,630; 4,183,914; 4,217,342, 4,217,343 and 5,093,387. U.S. Pat. No. 5,093,387 additionally proposes the use of the above mixed salts with an cationic gum, such as a synthetic guar gum salt. However, such denture adhesive compositions containing the copolymeric salts and/or cationic thickeners are found to be effective for only a limited time of not more than 8 hours and, in some instances, for as little as only 2–3 hours.

Accordingly it is an object of this invention to provide an improved adhesive composition which not only possesses extended holding power but also builds viscosity during use.

Another object is to provide an improved adhesive composition which is economical, easily prepared and which can be readily processed in commercial blending equipment.

These and other objects of this invention will become apparent from the following description and disclosure.

THE INVENTION

In accordance with this invention, there is provided an improved adhesive composition consisting essentially of (a) from about 10 to about 35 wt. % lower alkyl* vinyl ether-maleic acid copolymer wherein from about 0 to about 90% of the carboxyl units in the copolymer are converted to a mixture of metal salts, which metals are selected from the group of calcium, sodium, strontium, zinc, magnesium and potassium; (b) a non-ionic, natural crosslinked guar gum in a weight ratio of between about 0.75:1 and about 5:1 with respect to total copolymer; and (c) from about 30 to about 70 wt. % of an oil base as a carrier. * lower alkyl as used herein is intended to mean alkyl containing from 1 to 4 carbon atoms.

The copolymer of the present composition has a number average molecular weight of between about 500,000 and about 3,000,000 and is defined as containing the repeating structure

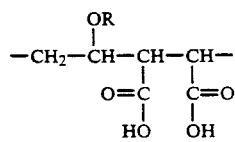

or

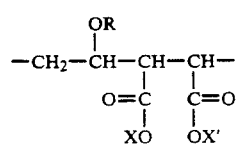

or a mixture thereof wherein R is $C_1$ to $C_4$ alkyl and one of X and X' is hydrogen and the other is selected from the group of Ca, Na, Zn, Sr, Mg and K to form a metal salt mixture or a maleic acid/lower alkyl vinyl ether copolymer.

Preferred of this group is the methyl vinyl ether-maleic acid copolymer having a number average molecular weight of between about 700,000 and about 2,000,000 wherein from 0.1 to 80% of the copolymer carboxyl units are converted to metal salt. The present copolymers from which the copolymeric salt mixtures may be derived are commercially available as GANTREZ® AN 149, 169 and 179, supplied by International Specialty Products. Most preferred of the mixed salts is the Ca/Na mixed salt.

In the present composition, the use of natural crosslinked guar gum in the above concentrations is critical to extended holding power and viscosity building properties. Although other gums have been used in denture adhesives, these products do not achieve the present desirable properties; additionally, they are objectionable for other reasons. For example, a karaya gum lacks chemical consistency, tragacanth gum undergoes interactions which destroy viscosity and acacia gum, although a good surfactant, is a poor thickening agent. While cationic guar gums have been used in denture adhesives, they have an objectionable amino flavor and exhibit a rapid drop-off in holding power. Natural guar gum is highly effective; however it is necessary to use excess amounts with respect to copolymer. It has now been found that the present crosslinked natural guar gums have none of the above disadvantages.

Natural, non-crosslinked guar gum having the formula

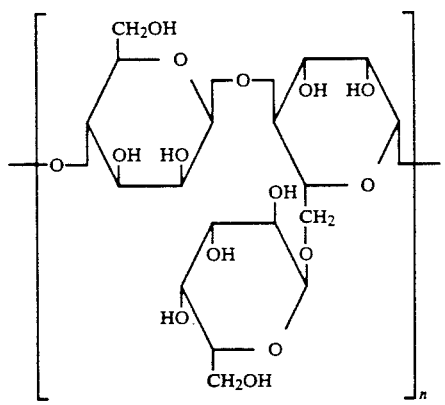

is a high molecular weight hydrocolloidal galactomannan polysaccharide having a Brookfield viscosity of between about 2,500 and about 8,000 cps in a one percent aqueous solution.

Guar gum is crosslinked by reacting the natural gum with an inorganic borate salt, such as calcium or sodium borate under ambient conditions in aqueous solution. The reaction product is between about 0.5 and about 10%, preferably between about 1 and about 7%, crosslinked through the boron atoms.

Generally, the Guar gum component comprises between about 12 and about 60 wt. %, preferably between about 20 and about 40 wt. % of the present composition and is employed in a weight ratio of at least 0.75:1 with regard to total polymer content. It has been found that the borate crosslinked natural guar gum has significantly greater thickening power than the non-crosslinked species. The most preferred ratio of polymer to guar gum is between about 1:0.9 and about 1:2.5.

The oil base employed as a carrier in the present composition can be any of the conventional oils suitable for medicinal purposes, including petrolatum, mineral oil, vegetable oils such as those derived from corn, soybean, cottonseed, castor bean, palm and coconut, as well as animal oils such as fish oil and oleic acid and mixtures thereof. The preferred carriers for this invention are mineral oil and petrolatum.

Because of the viscosity building properties of instant crosslinked natural guar gums, conventional thickeners such as carboxy methyl cellulose and the like can be eliminated or at least reduced, thus simplifying formulation. However, it is to be understood that various inactive excipients such as conventional flavoring agents, colorants, preservatives, sweetening agents and the like may be included in the overall formulation.

Preservatives which may be used in the denture adhesive formulations of the invention include those known antimicrobial agents conventionally employed in the art, such as benzoic acid and sodium benzoate; the parabens; sorbic acid and sorbates; propionic acid and propionates; acetic acid and acetates; nitrates and nitrites; sulfur dioxide and sulfites. The parabens include the methyl, ethyl, propyl, and butyl esters of parahydroxybenzoic acid. Methyl paraben and propyl paraben are the preferred preservatives of the invention, preferably utilized in amounts of about 0.03% to about 0.6% by weight of the total denture adhesive composition.

Sweetening agents are optionally employed and may be selected from a wide range of materials including water-soluble agents, water-soluble artificial sweeteners, and dipeptide based sweeteners, including mixtures thereof. Without being limited to particular sweeteners, representative illustrations encompass:

A. Water-soluble sweetening agents such as monosaccharides, disaccharides and polysaccharides such as xylose, ribose, glucose, mannose, galactose, fructose, dextrose, sucrose, sugar, maltose, partially hydrolyzed starch, or corn syrup solids and sugar alcohols such as sorbitol, xylitol, mannitol, maltitol, hydrogenated starch hydrolysate and mixtures thereof.

B. Water-soluble artificial sweeteners such as the soluble saccharin salts, i.e., sodium or calcium saccharin salts, cyclamate salts, acesulfame-K, sucralose and the like, and the free acid form of saccharin.

C. Dipeptide based sweeteners such as L-aspartyl-L-phenylalanine methyl ester and materials described in U.S. Pat. No. 3,491,131, L-D-aspartyl-N-(2,2,4,4-tetramethyl-3-thietanyl-D-alaninamide hydrate) and the like.

In general, the amount of sweetener when used will vary with the desired amount of sweetener selected for a particular denture adhesive formulation. This amount may be about 0.001% to about 5% by weight of the final denture adhesive composition when using an easily extractable sweetener.

Colorants may also be used in the present invention and include pigments such as titanium dioxide or dyes suitable for food, drug and cosmetic applications. These colorants are known as F.D. & C. dyes. The materials acceptable for the foregoing spectrum of use are preferably water-soluble. Illustrative examples include indigo dye, known as F.D. & C. Blue No. 2, which is the disodium salt of 5,5,-indigotindi-sulfonic acid. Similarly, the dye known as F.D. & C. Green No. 1, comprises a triphenylmethane dye and is the monosodium salt of the 4-[4N-ethyl-p-sulfobenzylamino) diphenylmethylene]-[1-N-ethyl-N-P-sulfo-benzyl)-2, 5-cyclohexadienimine]. Another useful colorant is F.D. & C. Red No. 3. A full recitation of F.D. & C. and D. & C. colorants and their corresponding chemical structures may be found in the *Kirk-Othmer Encyclopedia of Chemical, Technology*, 3rd Edition, in Volume 6, at pages 561–595.

Excipient additives are employed in small amounts of from about 0.001 to about 5 wt. % of the total composition.

The present adhesive compositions can be prepared by any of several well-known procedures. One process which is particularly recommended for the preparation of the present adhesive composition involves heating the oil base to a temperature of from about 170° to about 220° F., preferably a temperature of from about 80° to about 200° F., in a blender. Adding excipients to the hot oil base and then blending in the mixture the desired portion of gum at a temperature of from about 160° to about 210° F., preferably from about 180° to about 190° F. The resulting mixture is then stirred until a uniform dispersion is achieved, usually within a period of from five to thirty minutes, more often not more than fifteen minutes.

The desired amount of copolymer is then added to the dispersion at a temperature of from about 50° to about 190° F., preferably from about 165° to about 170° F., and mixing is continued until the components are uniformly blended, usually within a period of from about 10 to about 60 minutes, more often within a period of from 20 to 35 minutes. The blended copolymer mixture is then stirred for an additional period at a temperature of from about 150° to about 180° F., preferably from about 155° to about 165° F. After a uniform mixture is achieved, with continuous mixing, the dispersion is cooled to between about 50° and about 100° F., preferably to about room temperature, to form a cream-like gel with superior holding and viscosity building properties. It is to be understood that the initial viscosity of the present adhesive can be adjusted by regulating the amount of oil carrier or thickener employed.

Having generally described the invention, reference is now had to the following examples which illustrate preferred embodiments but are not to be construed as limiting to the scope of the invention as more broadly defined above and in the appended claims.

EXAMPLES 1–9

The following adhesive compositions were prepared by blending the mixture of petrolatum and mineral oil at 190° F. under agitation in a blender. To this mixture was added dry natural guar gum or a preformed dry blended mixture of natural guar gum and Na CMC (Na carboxymethyl cellulose) and mixed therein for about 10 minutes at 185° F. to form a dispersion. This was followed by feathering into the dispersion at about 170° F. the designated amount of methyl vinyl ether-maleic acid (50/50) copolymer in which 32% of the carboxyl groups were converted to the sodium salt and 48% converted to the calcium salt of the maleic acid units with 20% free acid. After copolymer addition was completed, the resulting mixture was stirred for an additional 30 minutes at 160° F. and a uniform dispersion of components was achieved. Finally the dispersion was gradually cooled to room temperature while stirring until a cream-like gel was formed.

In Examples 5, 6 and 7 the natural guar gum additive in a 1% or 5% aqueous solution was crosslinked with sodium borate at 72° F. over a period of 5 minutes. The resulting crosslinked guar gel was then dried under vacuum at 212° F. for 10 minutes to less than 10% moisture and ground to a powder before introducing into the formulation.

The composition of these gels is reported in following Table I.

TABLE I

| Example | 1 | 2 | 3 | 4 | 5 | 6 | 7 | 8 | 9 |
|---|---|---|---|---|---|---|---|---|---|
| | | | | | weight % | | | | |
| Light Mineral Oil USP | 16.0 | 16.0 | 16.0 | 16.0 | 19.0 | 19.0 | 19.0 | 19.0 | 19.0 |
| White Petrolatum USP | 30.4 | 30.4 | 30.4 | 30.4 | 19.0 | 19.0 | 19.0 | 19.0 | 19.0 |
| Na CMC | 24.0 | — | — | — | — | — | — | — | — |
| MVE-MA Copolymer (GANTREZ AN 169) Salt Mixture | 29.6 | 29.6 | 14.6 | 22.0 | 31.0 | 31.0 | 18.6 | 31.0 | 18.6 |
| Powdered Natural Guar | — | 24.0 | 39.0 | 31.6 | — | — | — | 31.0 | 43.4 |
| Crosslinked Guar | | | | | 31.0$^{(1)}$ | 31.0$^{(2)}$ | 43.4$^{(2)}$ | — | — |

Figure 2:
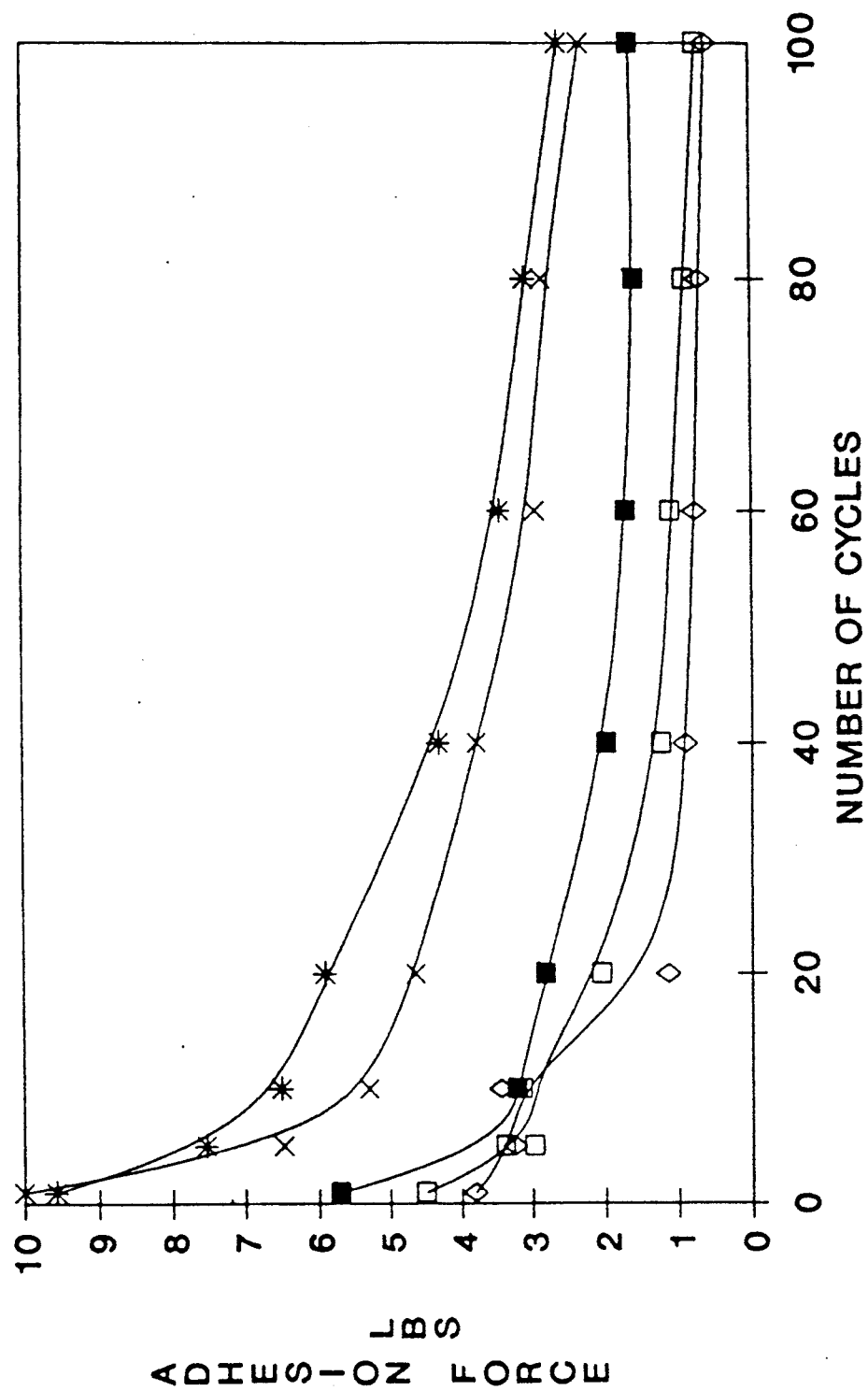

$^{(1)}$crosslinked with 5% sodium tetraborate
$^{(2)}$crosslinked with 1% sodium tetraborate The extended holding power and viscosity retaining properties of the above adhesive guar compositions were measured by Instron Adhesion and tube squeeze tests as shown in FIG. 1 for Examples 1, 2, 3 and 4 and in FIG. 2 for Examples 5, 6, 7, 8 and 9. The superiority of the crosslinked guar is shown by a comparison of Examples 5-7 with 2-4 and 8-9.

In FIG. 1, the curve for Example 1 is indicated by symbol
In FIG. 1, the curve for Example 2 is indicated by symbol X
In FIG. 1, the curve for Example 3 is indicated by symbol *
In FIG. 1, the curve for Example 4 is indicated by symbol □
In FIG. 2, the curve for Example 5 is indicated by symbol
In FIG. 2, the curve for Example 6 is indicated by symbol X
In FIG. 2, the curve for Example 7 is indicated by symbol *
In FIG. 2, the curve for Example 8 is indicated by symbol □
In FIG. 2, the curve for Example 9 is indicated by symbol Superior adhesion properties of crosslinked natural guar gum compositions over non-crosslinked guar is evidenced by the stronger holding power.

TUBE SQUEEZE TEST

The tube squeeze test on Examples 4-6 was carried out as described by B. Noren in the Journal of the Society of Cosmetic Chemistry 27, pages 47-61, 1976, entitled A METHOD TO EVALUATE THE TUBE SQUEEZING PROPERTIES OF TOOTHPASTE. Specifically, this test method comprises taking a 40 g. sample of the composition and filling a 1 inch diameter GLAMINATE ® tube (American National Can Corp.) having a 0.39 inch length and having a 0.168 inch diameter orifice. Then pressing the tube with a 1 inch circular piston exerting 10 psig for exactly 5.000 seconds. The grams of extruded sample indicate moldability of the gel. Extrusions between about 5 g. and 10 g. indicate good moldability and was met by all of the compositions of the present invention.

INSTRON STUDIES FOR ADHESION

A small amount (~2 g.) of denture adhesive is subjected to cyclic compressive and tensile stresses between two polymethylmethacrylate plates.

The first step in running this test is to bring the plates together to obtain the zero position (A). The upper plate is then raised 0.06 inch and the upper cycle limit on the Instron is set at this point (B). The upper plate is then lowered and the lower cycle limit is set (C) In its lowest position, then, the upper plate is 0.03 inch from the lower plate.

With these Instron settings determined, the upper plate was then raised high enough to spread 2 grams of sample uniformly over the top of the lower plate. Then 200 ml of simulated salivary fluid was added so that the sample was barely covered. The Instron crosshead was cycled between the set limits at a crosshead speed of 0.1 in./min. to record the compression and adhesion force for each cycle up to 100 cycles.

At the end of 100 cycles, the upper plate motion was halted and the plate cleaned. The apparatus was thoroughly washed and dried in preparation for the next denture adhesive evaluation.

The saliva solution was changed for each denture adhesive. Each recording was analyzed and the adhesional forces (lbs.) for the 1st, 5th, 10th, 15th . . . 100th cycles were recorded.

Extended holding power is generally measured between 60-100 cycles. Initial gel tackiness is measured between 0 and 60 cycles. It is desirable that initial tack should be above 1.5 on the graph.

In the above, Examples 2-4 are comparative and show that when non-crosslinked guar is not used in excess, viscosity building properties are absent; whereas the crosslinked guar achieves superior hold and viscosity retaining properties with equal amounts of polymer. Example 1 is also comparative and shows that when guar gum is entirely omitted, the composition lacks both extended holding power and also viscosity building properties.

COMPARISON OF EXAMPLES 10 and 11

Figure 3:
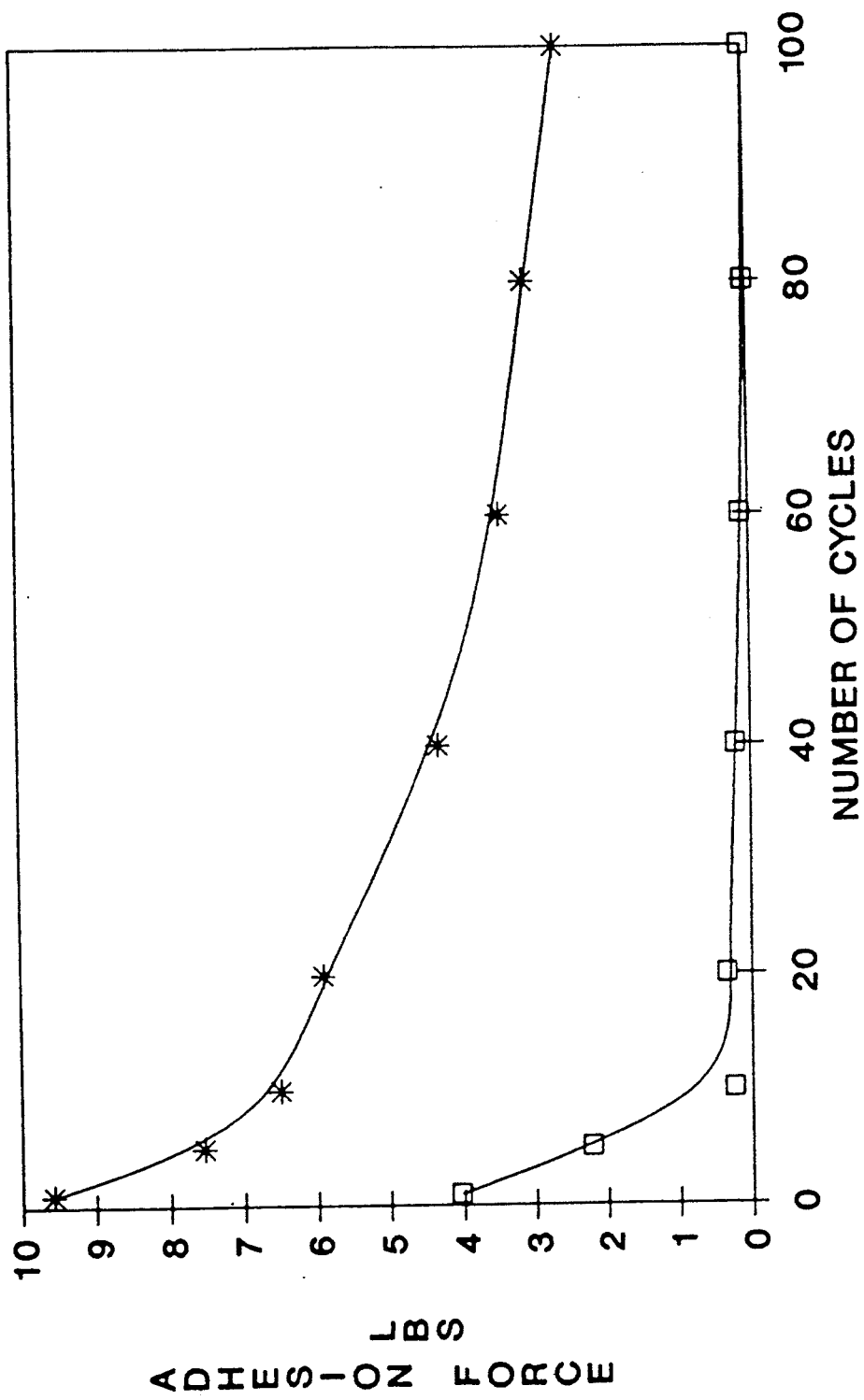

The compositions reported in following Table II are prepared as described for the above examples and then evaluated for tube squeezability, holding power and viscosity building properties which are compared and illustrated in FIG. 3. Example 10 represents the formulation used in U.S. Pat. No. 5,093,387 and indicated by the symbol □. Example 11 is indicated by the symbol *.

TABLE II

| Example Components | 10 Wt. % | 11 Wt. % |
|---|---|---|
| Light Mineral Oil USP | 19.0 | 19.0 |
| White Petrolatum USP | 20.0 | 19.0 |
| MVE/MA Copolymer Na/Ca Salt | 28.0 | 18.45 |
| Na carboxymethylcellulose | 15.0 | — |
| Na Cationic guar gum | 15.0 | — |
| Natural crosslinked guar | — | 43.4 |
| Preservatives (methyl/propyl paraben) | 0.15 | 0.15 |
| Fumed Silica | 1.0 | — |

TABLE II-continued

| Example Components | 10 Wt. % | 11 Wt. % |
|---|---|---|
| Ethylene Oxide Polymer | 1.85 | — |

As shown in FIG. 3, the holding power of the 5,093,387 patent formulation drops off sharply within the first 20 cycles and has short holding time; whereas the adhesive of the present invention has a greatly extended holding time as shows good retention of viscosity over 10 to 100 cycles.

Similar results were obtained when Examples 1 and 2 of the 5,093,387 patent were compared with the above natural crosslinked guar adhesive. Clearly, the use of natural crosslinked guar gum with mixed salt copolymer is greatly superior to the composition containing cationic guar gum.

Figure 4:
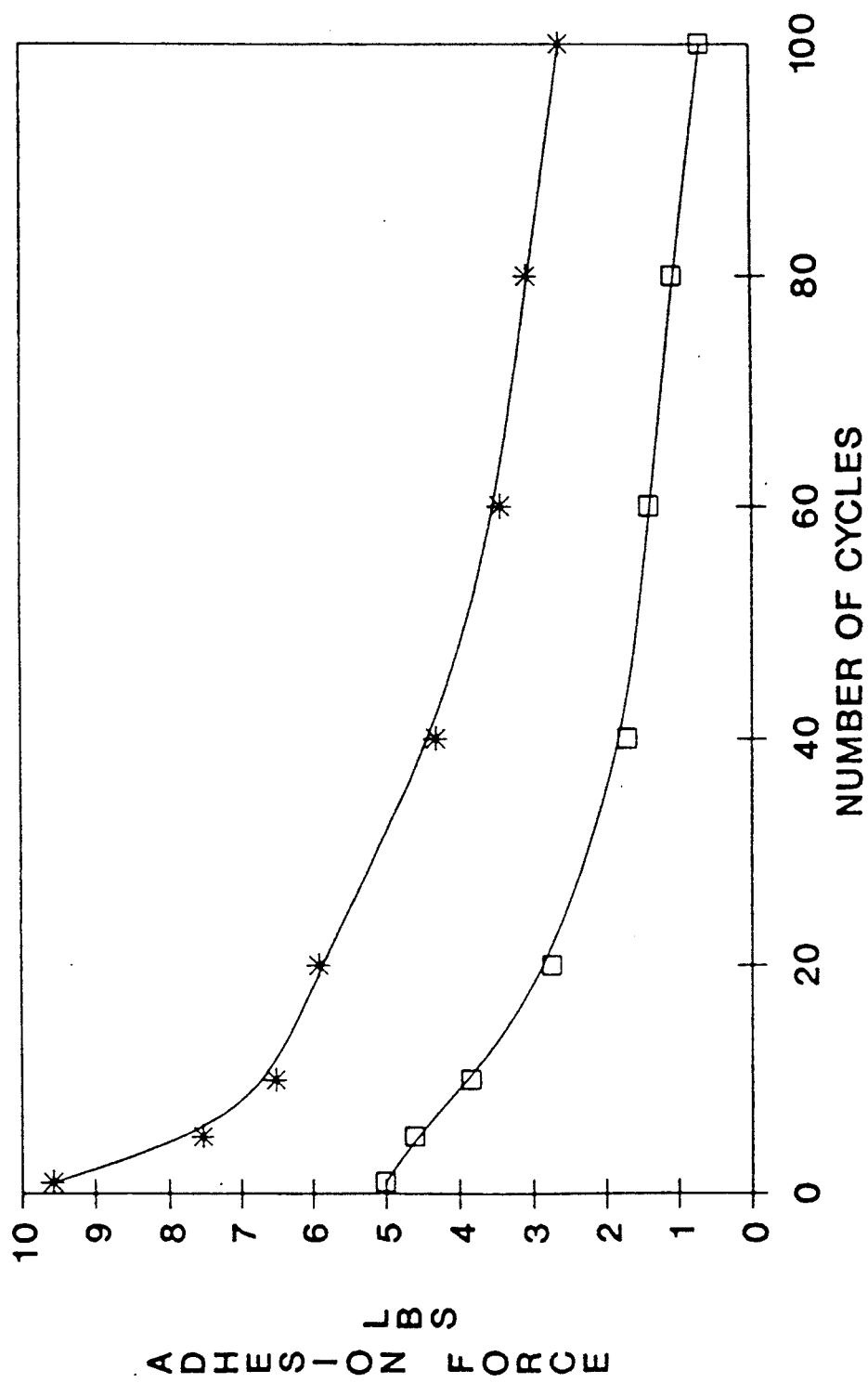

FIG. 4 illustrates the increased holding power and extended effectiveness of the crosslinked guar of Example 7 indicated by symbol *, as compared with the commercial denture adhesive FIXODENT indicated by symbol □.

The present invention having been described in the above examples and illustrated in FIGS. 1-3, defines preferred embodiments; however, it will become apparent that many modifications and variations in foregoing Examples 5-7 and 11 can be made without departing from the scope of this invention.

What is claimed is:

1. An improved denture adhesive composition having extended holding time and viscosity retaining properties consisting essentially of (a) from about 10 to about 35 wt. % lower alkyl vinyl ether-maleic acid copolymer wherein from about 0 to about 90 wt. % of the carboxyl units in the polymer is converted to a mixture of metal salts, which metals are selected from the group consisting of calcium, sodium, strontium, zinc, magnesium and potassium, (b) a natural-boron crosslinked guar gum in a weight ratio of between about 0.75:1 and about 5:1 with respect to said copolymer of component (a) and (c) from about 30 to about 70 wt. % of an oil carrier.

2. The composition of claim 1 wherein said polymer has a number average molecular weight of between about 500,000 and about 3,000,000.

3. The composition of claim 2 wherein said lower alkyl vinyl ether is methyl vinyl ether has a number average molecular weight of from about 700,000 to about 2,000,000.

4. The composition of claim 1 wherein between about 0.1 and about 80% of the carboxyl groups in said polymer are converted to a metal salt mixture.

5. The composition of claim 4 wherein said copolymer metal salt is a mixture of sodium and calcium salts.

6. The composition of claim 1 wherein the carboxyl groups of said copolymer are not converted to a metal salt.

7. The composition of claim 1 wherein said crosslinked guar gum is a solid gel.

8. The composition of claim 1 wherein between about 15 and about 60 wt. % of said guar gum is present in the composition.

9. The composition of claim 8 wherein the concentration of said guar gum in the composition is between about 24 and about 40 wt. %.

10. The composition of claim 1, wherein an inorganic borate is the crosslinking agent for said guar gum.

11. The composition of claim 1 wherein said oil carrier contains white petrolatum.

12. The composition of claim 1 wherein said oil carrier contains mineral oil.

13. The composition of claim 1 which additionally contains from about 0.001 to about 5 wt. % of an excipient such as a preservative, a flavoring agent, a colorant, a sweetener or a mixture thereof.

14. The composition of claim 13 wherein said composition contains from about 0.1 to about 0.5 wt. % of a preservative.

15. The composition of claim 1 wherein the weight ratio of said copolymer to said guar gum is from about 1:0.9 to about 2.5:1.

16. The denture composition of claim 15 which is a cream-like gel.

17. The composition of any one of claims 1, 4, 6, 8, 13 or 15 which is coated in an effective denture holding amount on the mucous membrane bonding surface of a denture.

* * * * *